United States Patent [19]

Ichikawa et al.

[11] Patent Number: 5,147,902

[45] Date of Patent: Sep. 15, 1992

[54] ULTRAVIOLET LIGHT ABSORBING OCULAR LENS

[75] Inventors: Makoto Ichikawa; Kazuharu Niwa; Kazuhiko Nakada, all of Nagoya, Japan

[73] Assignee: Menicon Co., Ltd., Nagoya, Japan

[21] Appl. No.: 798,205

[22] Filed: Nov. 26, 1991

[30] Foreign Application Priority Data

Nov. 26, 1990 [JP] Japan .................................. 2-323835

[51] Int. Cl.$^5$ ........................................... C07D 249/20
[52] U.S. Cl. ..................... 523/106; 514/972; 524/94; 526/259; 548/259
[58] Field of Search ................ 523/106; 524/94; 514/972; 548/259

[56] References Cited

U.S. PATENT DOCUMENTS

| | | | |
|---|---|---|---|
| 4,528,311 | 7/1985 | Beard et al. | 548/259 |
| 4,611,061 | 9/1986 | Beard et al. | 548/259 |
| 4,716,234 | 12/1987 | Dunks et al. | 548/259 |
| 4,863,802 | 9/1989 | Moore et al. | 548/259 |
| 5,084,537 | 1/1992 | Stoyan | 523/106 |

FOREIGN PATENT DOCUMENTS 60-38411 2/1985 Japan.
63-185969 8/1988 Japan.

*Primary Examiner*—Paul R. Michl
*Assistant Examiner*—Andrew E. C. Merriam
*Attorney, Agent, or Firm*—Oblon, Spivak, McClelland, Maier & Neustadt

[57] ABSTRACT

An ultraviolet light absorbing occular lens comprising a vinyl type copolymer containing from 0.01 to 0.5% by weight of a benzotriazole type ultraviolet light absorbing monomer as chemically bonded therewith, the ultravioleet light absorbing monomer having the formula:

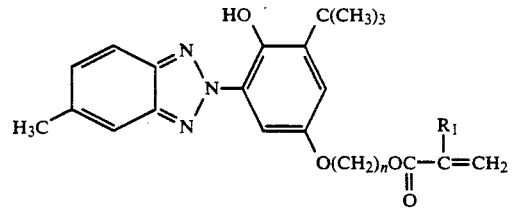

(wherein $R_1$ is H or $CH_3$ and n is 2 or 3).

9 Claims, 1 Drawing Sheet

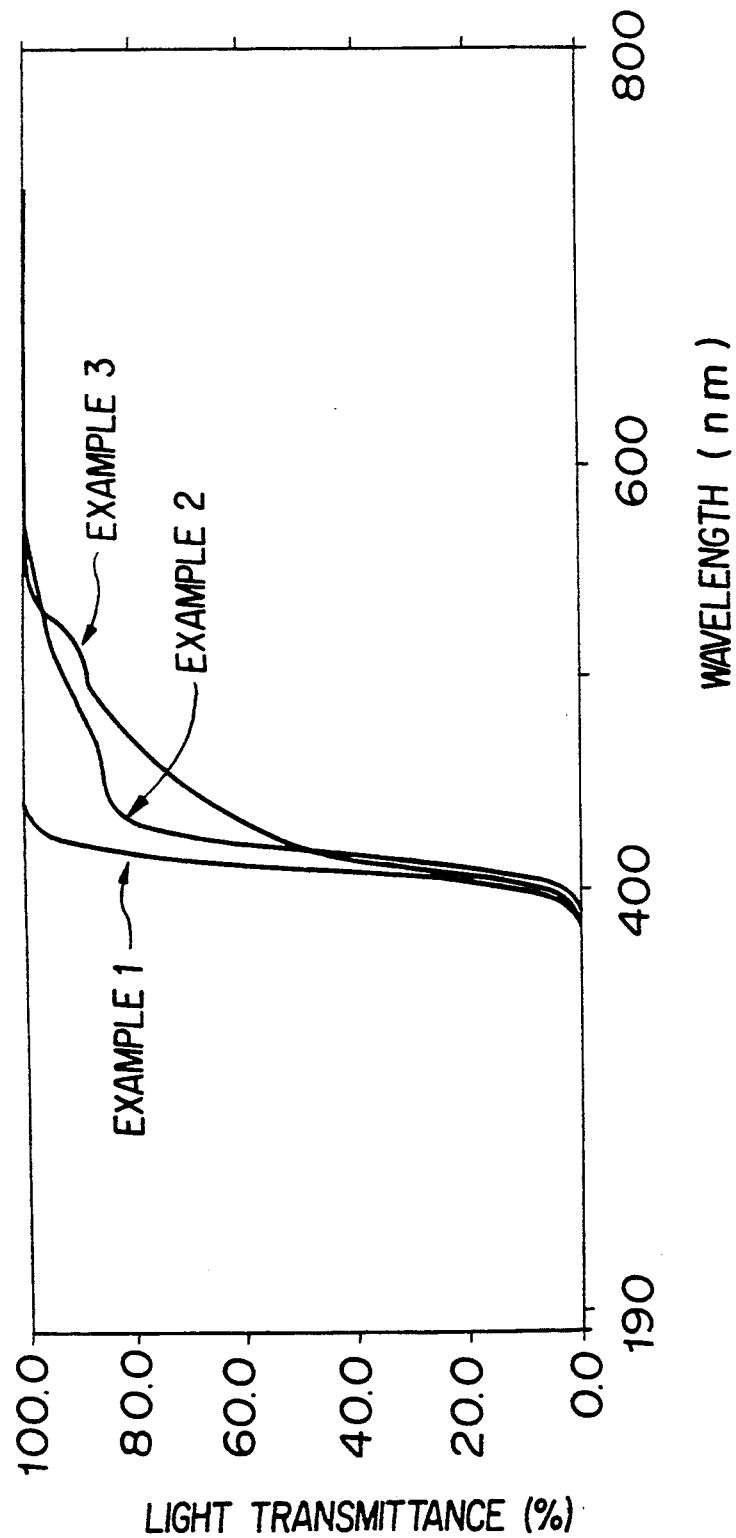

ULTRAVIOLET LIGHT ABSORBING OCULAR LENS

The present invention relates to an ocular lens such as an intraocular lens and a contact lens, which is excellent in ultraviolet light absorbing properties and which has optical properties similar to those of the human crystalline lens.

After removing the human crystalline lens by operation to cure cataract, ocular lenses for accommodating the sight such as an intraocular lens and a contact lens are generally used for recovering the sight. However, these artificial ocular lenses do not have properties inherent in the natural human crystalline lens, i.e. the property to intercept ultraviolet light. Therefore, there is a fear that ultraviolet light which should be naturally absorbed by the human crystalline lens reaches the retina and damages it.

Also, generally, the human crystalline lens is colored and turned yellow in proportion as getting old. The color sense through such colored human crystalline lens is different from the color sense through artificial ocular lenses comprising transparent polymer materials such as methylmethacrylate, and this difference in the color sense often gives unpleasant feeling to a patient.

Accordingly, in recent years, there have been proposed and studied ocular lenses having properties of absorbing ultraviolet light or containing coloring matters in (1) Japanese Unexamined Patent Publication No. 38411/1985 (USP 4,611,061), (2) Japanese Unexamined Patent Publication No. 185969/1988 (USP 4,716,234), (3) Japanese Unexamined Patent Publication No. 299560/1989 and (4) Japanese Unexamined Patent Publication No. 63463/1990.

However, these proposed ocular lenses are not preferable particularly for medical use since they have problems such as deterioration and elution. That is, the ultraviolet light absorbing agent having the formula,

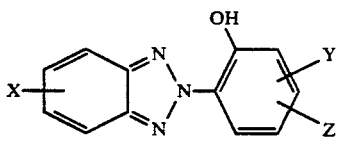

disclosed in these references, are unstable and liable to be decomposed, for example, when X is Cl in the formula of the above reference (1), when X is an alkoxy group having carbon atoms of 1 to 3 in the formula of the above reference (2), when X is a halogen (Cl) in the formula of the above reference (3), and when X is an alkoxy group (—OCH$_3$) in the formula of the above reference (4).

The present invention has been made under the above-mentioned circumstances, and an object of the present invention is to provide a useful ocular lens having an excellent ultraviolet light absorbing property suitable for medical use by using an ultraviolet absorbing monomer having a high stability which can be easily synthesized at a high purity.

Thus, the present invention is to solve the above-mentioned problems, and the essential feature of the present invention resides in an ultraviolet light absorbing ocular lens comprising a vinyl type copolymer containing from 0.01 to 0.5% by weight of a benzotriazole type ultraviolet light absorbing monomer as chemically bonded therewith, said ultraviolet light absorbing monomer having the formula (I):

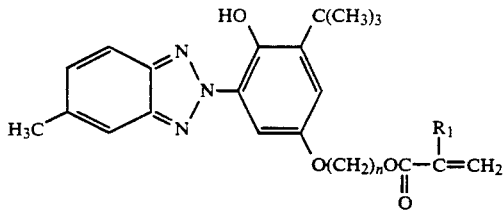

(wherein R$_1$ is H or CH$_3$ and n is 2 or 3).

The ultraviolet light absorbing ocular lens of the present invention is preferably an intraocular lens which comprises a vinyl type copolymer containing from 0.01 to 0.5% by weight of a benzotriazole type ultraviolet light absorbing monomer of the above formula (I) as chemically bonded therewith and from 0.0001 to 0.1% by weight of a coloring matter.

FIG. 1 shows graphs illustrating the light-transmissive properties of the intraocular lenses prepared by using the respective polymers obtained in Examples 1 to 3.

The ultraviolet light absorbing monomer to be copolymerized with the vinyl type copolymer constituting the ocular lens of the present invention is a benzotriazole type monomer having the above formula (I), examples of which include 2-[2'-hydroxy-5'-(β-methacryloyloxyethoxy)-3'-t-butylphenyl]-5-methyl-2H-benzotriazole (UV1) (wherein n in the formula (I) is 2) and 2-[2'-hydroxy-5'-(λ-methacryloyloxypropoxy)-3'-t-butylphenyl]-5-methyl-2H-benzotriazole (UV2) (wherein n in the formula (I) is 3).

Since these ultraviolet light absorbing monomers (such as UV1 and UV2) are polymerizable benzotriazole type monomers having high ultraviolet light absorbing properties, the desired effect can be favorably achieved by using these monomers in a small amount and there is provided an ocular lens of a high safety which does not elute the ultraviolet absorbing agent.

In the present invention, the ultraviolet light absorbing monomer is contained in an amount of from 0.01 to 0.5% by weight. If the content of the ultraviolet light absorbing monomer is less than 0.01% by weight, ultraviolet light is not satisfactorily intercepted. On the other hand, if the content of the ultraviolet light absorbing monomer is more than 0.5% by weight, it is not preferable in respect of solubility and safety.

The vinyl type copolymer used for preparing the ocular lens of the present invention can be applied to any of intraocular lenses, contact lenses and lenses for glasses. Depending on the aimed use of a lens, a vinyl type monomer used for constituting the vinyl type copolymer, is optionally selected from monomers giving rigid materials or monomers giving soft materials or in combination, in addition to the ultraviolet light absorbing monomer of the formula (I). These monomers are not specially limited, but any of commonly used monomers can be employed.

Concrete Examples of these monomers are listed below, but the term ". . . (meth)acrylate" means two types of compounds of ". . . acrylate" and ". . . methacrylate", and the term "(meth)acryl derivatives" means the same things in the same way.

Thus, there are enumerated linear chain-like, branched chain-like or cyclic alkyl (meth)acrylates such as methyl (meth)acrylate, ethyl (meth)acrylate, propyl (meth)acrylate, n-butyl (meth)acrylate, tert-butyl (meth)acrylate and isobutyl (meth)acrylate; fluorine-containing (meth)acrylates such as 2,2,2-trifluoroethyl (meth)acrylate, 2,2,3,3-tetrafluoropropyl (meth)acrylate, 2,2,3,3,3-pentafluoropropyl (meth)acrylate, 2,2,2-trifluoro-1-trifluoromethylethyl (meth)acrylate, 2,2,3,3-tetrafluoro-tert-pentyl (meth)acrylate and 2,2,3,4,4,4-hexafluorobutyl (meth)acrylate; silicon-containing (meth)acrylates such as pentamethyldisiloxanylmethyl (meth)acrylate, pentamethyldisiloxanylpropyl (meth)acrylate, methylbis(trimethylsiloxy)silylpropyl (meth)acrylate and tris(trimethylsiloxy)silylpropyl (meth)acrylate; styrene derivatives such as trimethylsilylstyrene, o-methylstyrene, m-methylstyrene, p-methylstyrene, p-ethylstyrene, o-hydroxystyrene, m-hydroxystyrene, p-hydroxystyrene, trimethylstyrene, tertbutylstyrene, perbromostyrene, dimethylaminostyrene and α-methylstyrene; fluorine-containing styrene derivatives such as 4-vinylbenzyl-2',2',2'-trifluoroethyl ether, 4-vinylbenzyl-2',2',3',3',4',4',4'-heptafluorobutyl ether and 4-vinylbenzyl-3',3',3'-trifluoropropyl ether; N-vinyllactams such as N-vinylpyrrolidone, α-methylene-N-methylpyrrolidone and N-vinylcaprolactam; 4-vinylpyridine; heterocyclic N-vinyl monomers such as vinylimidazol and N-vinylpiperidone; hydroxyl group-containing (meth)acrylates such as hydroxyethyl (meth)acrylate, hydroxypropyl (meth)acrylate and hydroxybutyl (meth)acrylate; (meth)acrylic acid; N-(meth)acryloylpyrrolidone; (meth)acryl amides such as (meth)acrylamide and N-methyl (meth)acrylamide; aminoalkyl (meth)acrylates such as aminoethyl (meth)acrylate and N-methylaminoethyl (meth)acrylate; alkoxy group-containing (meth)acrylates such as methoxyethyl (meth)acrylate and ethoxyethyl (meth)acrylate; aromatic ring-containing (meth)acrylates such as benzyl (meth)acrylate; glycidyl (meth)acrylate; diethyleneglycol bisallyl carbonate; 4,4-isopropylidenediphenyl bisallyl carbonate and the like.

From these monomers, one or more kinds of monomers are optionally selected, and the selected one or more monomers are polymerized to produce a macromonomer which can be used as a polymerizing component for preparing an ocular lens material.

These monomers are selected by considering the aimed properties of various ocular lenses to be produced. For example, in order to obtain a highly oxygen-transmissive material for a contact lens material, silicon-containing monomers such as silicon-containing (meth)acrylates and silicon-containing styrene derivatives, and fluorine-containing alkyl (meth)acrylates are preferably selected. Alternatively, in order to obtain a strong ocular lens material for reinforcing a lens, or to control the hardness of an ocular lens to be produced, alkyl (meth)acrylates, styrene derivatives including styrene, or (meth)acrylic acid are preferably selected.

Also, in order to make a lens resistant to staining with grease, fluorine-containing monomers such as fluorine-containing alkyl (meth)acrylates and fluorine-containing styrene derivatives are preferably selected. In order to impart hydrophilic nature to a lens or to obtain a soft type hydrous ocular lens, monomers having hydrophilic groups such as hydroxyl group-containing (meth)acrylates, (meth)acrylamides, aminoalkyl (meth)acrylates, (meth)acrylic acid and N-vinyl lactams are preferably selected. Furthermore, in order to obtain a highly refractive ocular lens, aromatic ring-containing monomers such as styrene type monomers and aromatic ring-containing (meth)acrylates are preferably selected.

A crosslinking agent may be added to these monomers or mixtures thereof as an optional component. The crosslinking agent provides such various effects by forming a three dimensional crosslinked structure in the polymer as to produce a uniform, transparent and cloudless ocular lens material of no stress having satisfactory optical properties. The ocular lens material thus produced is improved in various physical properties such as toughness, mechanical strength and hardness, and is also improved in chemical resistance, heat resistance, shape stability and durability by a crosslinking effect. Furthermore, a substance eluted from the ocular lens material can be remarkably reduced.

Any of commonly used crosslinking agents can be used as this crosslinking agent, concrete examples of which include 4-vinylbenzyl (meth)acrylate, 3-vinylbenzyl (meth)acrylate, ethylene glycol di(meth)acrylate, diethylene glycol di(meth)acrylate, allyl (meth)acrylate and the like. A macromonomer having at least 2 polymerizable groups in a molecule may also be used as a crosslinking agent. Among these, one or more types of crosslinking agents may optionally be selected, and are used in an amount of preferably from 0.1 to 5 parts by weight, more preferably from 1 to 4 parts by weight per 100 parts by weight of the total amount of all the polymerizable components. If the crosslinking agent is used in an amount exceeding the above range, the material obtained thereby becomes brittle and weak to impact stress. On the other hand, if the crosslinking agent is used in an amount of smaller than the above range, a satisfactory crosslinking effect can be achieved.

A polymerizable material prepared by optionally combining the above-mentioned monomers is polymerized to produce a polymer, i.e. a vinyl type copolymer for providing a desired ocular lens.

Polymerization can be conducted by various methods generally employed. For example, in the case of heat polymerization, a radical polymerization initiator is blended with a polymerizable material, and the polymerization is completed by raising a temperature from room temperature to 130° C. for about ten several hours. In the case of photopolymerization, a photopolymerization initiator is blended with a polymerizable material, and the polymerization of the resultant mixture is completed by irradiating light (for example, ultraviolet ray) having a wavelength corresponding to the absorption band of the photopolymerization initiator. Polymerization may be conducted by combining the above-mentioned heat polymerization with the photopolymerization. The heat polymerization may be conducted by heating in a constant temperature bath or a constant temperature chamber or by applying an electromagnetic wave such as microwave, and the heating may be effected stepwise. In the case of the photopolymerization, a sensitizer may further be added.

In the production of an ocular lens material, in order to efficiently produce the material, bulk polymerization method is preferable, but if necessary, solution polymerization method may be employed.

Examples of a polymerization initiator are illustrated hereinafter. Examples of a radical polymerization initiator include azobisisobutylonitrile, azobisdimethylvaleronitrile, benzoyl peroxide and the like. Examples of a photopolymerization initiator include benzoin type photopolymerization initiators such as benzoin, methylorthobenzoyl benzoate and methylorthobenzoin benzoate; phenone type photopolymerization initiators such as 2-hydroxy-2-methyl-1-phenylpropane-1-one and p-isopropyl-α-hydroxyisobutylophenone; 1-hydroxycyclohexylphenylketone; 1-phenyl-1,2-propandione-2-(o-ethoxycarbonyl).oxime; thioxanthone type photopolymerization initiators such as 2-chlorothioxanthone and 2-methylthioxanthone; dibenzosuberone; 2-ethylanthraquinone; benzophenone acrylate; benzophenone; benzil and the like. From these, one or more types of initiators are optionally selected and used in an amount of from about 0.001 to 5 parts by weight, preferably from 0.01 to 2 parts by weight per 100 parts by weight of the total amount of all the polymerizable components.

The ocular lens of the present invention can be satisfactorily used for an intraocular lens. Examples of a coloring matter to be contained in the intraocular lens include a coloring matter having a molar absorptivity of at least $2 \times 10^2$ at 480 nm and a coloring matter having $\lambda_{max}$ at 450 to 510 nm and a molar absorptivity of at least $2 \times 10^3$ at the $\lambda_{max}$.

In the present invention, any of known coloring matters may be used as such a coloring matter, and among these, orange or yellow oil-soluble and acidic dyes are preferably used. These coloring matters do not intercept light of 500 to 550 nm having influence on eyesight, but provide the same color as that of the human crystalline lens, thereby producing an intraocular lens having optical properties similar to those of the human crystalline lens and having no change in color sense.

Such a coloring matter provides a desired color at a low concentration, for example, from 0.0001 to 0.1% by weight, preferably from 0.01 to 0.05% by weight. If the content of the coloring matter is less than 0.0001% by weight, a desired color can not be obtained. On the other hand, if the content of the coloring matter is more than 0.1% by weight, the eyesight is lowered in the darkness due to the high concentration. Also, if a coloring matter having a molar absorptivity of less than $2 \times 10^2$ at 480 nm is used, the amount of the coloring matter must be unpreferably increased in order to obtain a desired color.

So long as the above-mentioned conditions are satisfied, any type of coloring matters including an ordinary coloring matter simply blended to develop color and a coloring matter chemically bonded with a lens-forming material by polymerization can be used. For example, such azo type coloring matters having safety and stability as listed in the following Table 1 can be satisfactorily used. The molar absorptivity of 1-phenylazo-4-methacryloyloxynaphthalene is a value at 480 nm, and the abbreviations in the Table respectively mean as follows:

| S: solvent | P: pigment |
| --- | --- |
| O: orange | Y: yellow |
| Br: brown | R: red |

In the present invention, the above-mentioned coloring matters are uniformly blended and copolymerized together with other monomers to be copolymerized when polymerizing a lens material, but depending on the type of the polymerizable materials used, the coloring matters may be incorporated into finally obtained polymer by impregnation without adding them to the polymerizable materials (regardless of occurrence of copolymerization).

TABLE 1

| Name of coloring matter | CI Name | λmax (nm) | Molar absorptivity |
| --- | --- | --- | --- |
| 2,4-dihydroxyazobenzene | CI—S—O-1 | 473 | $2.5 \times 10^4$ |
| 4-hydroxy-3-methylazobenzene | CI—S—Y-10 | 489 | $4 \times 10^4$ |
| 4-amino-3,2'-dimethylazobenzene | CI—S—Y-3 | 490 | $2.5 \times 10^3$ |
| 4-phenylazo-1-naphthol | CI—S—Br-4 | 490 | $1.5 \times 10^4$ |
| 4-(2'-methylphenylazo)-1-naphthol | CI—S—R-2 | 485 | $1.2 \times 10^4$ |
| 1-(2'-methylphenylazo)-2-naphthol | CI—S—O-2 | 480 | $1.5 \times 10^4$ |
| | | 500 | $1.5 \times 10^4$ |
| 1-(2'-methoxyphenylazo)-2-naphthol | CI—S—R-1 | 502 | $2 \times 10^4$ |
| | | 510 | $2.5 \times 10^4$ |
| 1-(2'-nitrophenylazo)-2-naphthol | CI—P—O-2 | 485 | $2 \times 10^4$ |
| | | 490 | $2 \times 10^4$ |
| 4,4'-diamino-1,1'-azonaphthalene | — | 490 | $2.5 \times 10^4$ |
| 1-phenylazo-4-methacryloyloxynaphthalene | — | — | $2 \times 10^3$ |
| 1-phenylazo-2-hydroxy-3-methacryloyloxynaphthalene | — | 490 | $2 \times 10^4$ |

As described above, the ocular lens of the present invention intercepts ultraviolet light (light of a wavelength not longer than 380 nm) and has optical properties quite similar to those of human eyes since the specific benzotriazole type ultraviolet light absorbing monomer bonded therein has a high stability and is easily synthesized at such a high purity as to provide excellent polymerizability and to satisfactorily maintain the safety of the lens.

Now, the present invention will be described in further detail with reference to Examples. However, it should be understood that the present invention is by no means restricted to such specific Examples.

Also, it should be understood that in addition to the above descriptions and following Examples, the present invention can be variously modified and improved by those skilled in the art without departing from the scope of the present invention.

REFERENCE EXAMPLE 1

Synthesis of
2-[2'-hydroxy-5'-(β-methacryloyloxyethoxy)-3'-t-butylphenyl]-5-methyl-2H-benzotriazole (UV1)

Preparation of intermediate,
[2-t-butyl-4-(2'-hydroxyethoxy)phenol]

332 g (2 mol) of t-butylhydroquinone and 1 g of potassium iodide were dissolved in 2 l of water under nitrogen atmosphere, and were heated to 80° C. Thereafter, to the solution thus obtained, were dropwise added 232 g (2.8 mol) of 48% sodium hydroxide aqueous solution and 200 g (2.5 mol) of ethylene chlorohydrine at the same time for 3 hours while constantly maintaining alkaline. After finishing this dropwise addition, the resultant reaction mixture was heated for 8 hours at the reflux temperature. After cooling the reaction mixture thus obtained, the reaction mixture was neutralized with sulfuric acid and was extracted with toluene. After removing solvent, the remaining material was distilled under reduced pressure and the distillate was recrystallized from toluene to obtain 200 g of 2-t-butyl-4-(2'-hydroxyethoxy)phenol. The reaction formula (alkylation) is illustrated in the following.

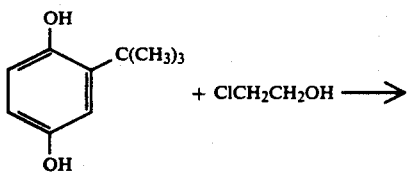

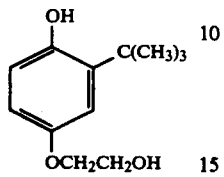

(B) Preparation of intermediate, [2-t-butyl-4-(β-hydroxyethoxy)-6 (4'-methyl-2'-nitrophenylazo)phenol 80 g (0.52 mol) of 4-methyl-2-nitroaniline, 400 ml of water and 200 g of concentrated hydrochloric acid were charged, and the mixture was stirred at room temperature for overnight and was then cooled to 0° C. To this mixture, was dropwise added at 0° to 5° C., a solution of 36.4 g (0.53 mol) of sodium nitrite dissolved in 80 ml of water. After finishing the dropwise addition, the mixture was stirred at 0° to 5° C. for 1 hour, and after filtrating, the remaining nitrous acid was decomposed by sulfamic acid.

On the other hand, 100 g (0.47 mol) of the product obtained in the above (A) step, 40 g (1 mol) of sodium hydroxide and 40 g (0.68 mol) of magnesium hydroxide were added in 400 ml of water, and were cooled to 0° C. To the mixture, was dropwise added the above prepared diazonium solution at 0° to 5° C. After finishing the reaction, the reaction mixture was acidified with hydrochloric acid, and was extracted with toluene. Thereafter, the reaction mixture was filtered to remove solvent, and was subjected to crystallization with methanol to obtain 70 g (0.19 mol) of 2-t-butyl-4-(β-hydroxyethoxy)-6-(4 -methyl-2'-nitrophenylazo)-phenol. The reaction formula (diazo coupling) is illustrated hereinafter.

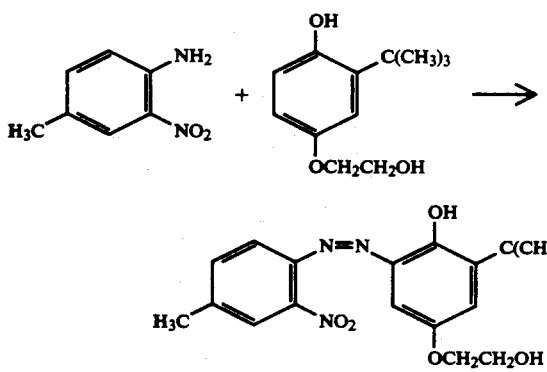

(C) Preparation of intermediate, [2-[2'-hydroxy-5'-(β-hydroxyethoxy)-3'-t-butylphenyl]-5-methyl-2H-benzotriazole-N-oxide]

70 g (0.19 mol) of the product obtained in the above (B) step, 200 ml of water, 100 ml of isopropyl alcohol, 20 g of sodium hydroxide and 0.2 g of hydroquinone were charged, and 20 μl of 80% hydrazine hydrate was dropwise added thereto at 70° C. After the dropwise addition, the mixture was stirred for 2 hours under refluxing, and after finishing the reaction, the reaction mixture was neutralized with sulfuric acid. Thereafter, after filtrating and then cooling, the crystal thus formed was taken out by filtration and was washed with water. The crystal thus obtained was used as it is in the following reaction without purification.

This oxide-forming reaction is illustrated hereinafter.

(B) Intermediate ⟶

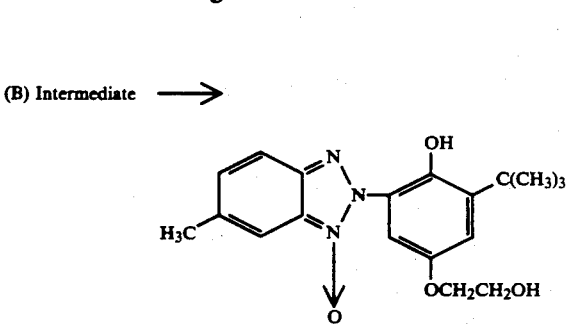

(D) Preparation of intermediate, [2-[2'-hydroxy-5'-(β-hydroxyethoxy)-3'-t-butylphenyl]-5-methyl-2H-benzotriazole]

60 g of the oxide obtained in the above (C) step, 150 ml of toluene, 90 ml of water, 100 ml of isopropyl alcohol and 40 g of concentrated sulfuric acid were charged, and 20 g of zinc powder was added thereto at 70° C. After finishing the reaction, the reaction product was classified and washed with water, and solvent was removed. Thereafter, after dissolving the product in toluene, the product was decolored by china clay and was subjected to crystallization to obtain 52 g (0.15 mol) of 2-[2'-hydroxy-5'-(β-hydroxyethoxy)-3'-t-butylphenyl]-5-methyl-2H-benzotriazole. The triazole-forming reaction is illustrated hereinafter.

(C) Intermediate 

[Structure diagram showing benzotriazole product]

(E) Preparation of 2-[2'-hydzoxy-5'-(β-methacryloyloxyethoxy)-3'-t-butylphenyl]-5-methyl-2H-benzotriazole 50 g (0.15 mol) of benzotriazole prepared in the above step (D) and 25 g of pyridine were dissolved in 1,000 ml of toluene, and 17.5 g (0.17 mol) of newly distilled methacryloyl chloride was dropwise added thereto at 20° to 25° C. After this dropwise addition, the mixture was stirred at 20° to 25° C. for 10 hours, filtrated, washed with water and then solvent was removed. The resultant product was subjected to crystallization from 200 ml of toluene and 500 ml of isopropyl alcohol to obtain 48 g (0.12 mol) of 2-[2'-hydroxy-5'-(β-methacryloyloxyethoxy)-3'-t-butylphenyl]-5-methyl-2H-benzotriazole having a purity of 98%. This esterification reaction is illustrated hereinafter.

(D) Intermediate + ClCC=CH₂ (with O double bond and CH₃) →

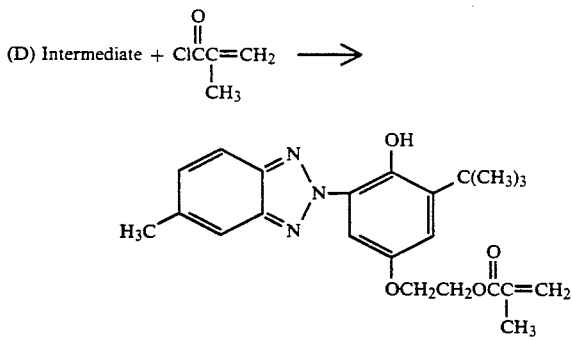

REFERENCE EXAMPLE 2

Synthesis of 2-[2'-hydroxy-5'-(λ-methacryloyloxypropoxy)-3'-t-butylphenyl]-5-methyl-2H-benzotriazole (UV2)

The above monomer (UV2) was synthesized in the same manner as in the synthesis of the above UV1 in the step (A), except that 237 g (2.5 mol) of propylene chlorohydrine was used in place of ethylene chlorohydrine.

EXAMPLES 1 TO 3

Compositions comprising such ingredients as described in the following Table 2 were placed respectively in glass test tubes, and the test tubes were stoppered tightly.

The compositions were respectively prepolymerized at 35° C. for 40 hours in a constant temperature water tank, and the test tubes were placed in a circulatory dryer where the polymerizable materials in the test tubes were heat-polymerized by heating at 50° C. for 8 hours, raising temperature to 130° C. for 2 hours and further heating at 110° C. for 1 hour to remove stress, thereby producing three types of bar-like vinyl type copolymers.

The copolymers thus obtained were cut and were subjected to mechanical processing by cutting and polishing to obtain lenses for glasses having a thickness of 2 mm (test pieces). With regard to the test pieces thus obtained, light-transmissive properties were measured, and the results are shown in FIG. 1.

As evident from these results, the lenses for glasses thus obtained were proved to have optical properties similar to those of the human crystalline lens.

TABLE 2

| Example | | 1 | 2 | 3 |
|---|---|---|---|---|
| Monomer | MMA | 97 | 97 | 99 |
| Crosslinking agent | EDMA | 3 | 3 | 1 |
| Ultraviolet light absorbing monomer | UV1 | 0.125 | 0.125 | — |
|  | UV2 | — | — | 0.125 |
| Coloring matter | α-4BM | — | 0.02 | — |
|  | Yellow No. 402 | — | — | 0.01 |
|  | CI—S—O-2 | — | — | 0.00092 |
| Polymerization initiator | AIBN | 0.1 | 0.1 | 0.1 |

Unit: Parts by weight

The abbreviations described in the above Table 2 stand for the following meanings.

MMA: methyl methacrylate
EDMA: ethylene glycol dimethacrylate
UV1: 2-[2'-hydroxy-5'-(β-methacryloyloxyethoxy)-3'-t-butylphenyl]-5-methyl-2H-benzotriazole
UV2: 2-[2'-hydroxy-5'-(λ-methacryloyloxypropoxy)-3'-t-butylphenyl]-5-methyl-2H-benzotriazole
α-4BM: 1-phenylazo-4-methacryloylnaphthalene
Yellow No. 402: legal coloring matter
CI-S-O-2: 1-(2'-methylphenylazo)-2-naphthol
AIBN: azobisisobutyronitrile With regard to a molar absorptivity of each coloring matter, α-4BM has a molar absorptivity of $2 \times 10^3$ at 480 nm and CI-S-O-2 has a molar absorptivity of $1.5 \times 10^4$ at 480 nm.

As described above, the specific benzotriazole type ultraviolet light absorbing monomers to be bonded in the ultraviolet light absorbing ocular lens of the present invention are easily synthesized at a high purity and have excellent stability and polymerizability. Thus, the ocular lens of the present invention comprising a vinyl type copolymer containing a specific amount of such a monomer bonded therewith, has various advantages that the ultraviolet light absorbing agent is not substantially eluted from the lens, thus having a high safety, that its stability is excellent, thus no deterioration being caused, and that its optical properties are similar to those of the human crystalline lens. Accordingly, the ultraviolet light absorbing ocular lens of the present invention is quite suitable for a medical intraocular lens, a contact lens and the like.

We claim:

1. An ultraviolet light absorbing ocular lens comprising a vinyl type copolymer containing from 0.01 to 0.5% by weight of a benzotriazole type ultraviolet light absorbing monomer as chemically bonded therewith, said ultraviolet light absorbing monomer having the formula:

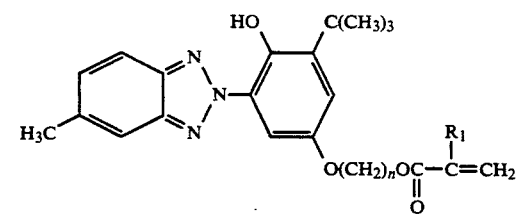

(wherein $R_1$ is H or $CH_3$ and n is 2 or 3).

2. The ultraviolet light absorbing ocular lens according to claim 1, wherein said ultraviolet light absorbing monomer is 2-[2'-hydroxy-5'-(β-methacryloyloxyethoxy)-3'-t-butylphenyl]-5-methyl-2H-benzotriazole.

3. The ultraviolet light absorbing ocular lens according to claim 1, wherein said ultraviolet light absorbing monomer is 2-[2'-hydroxy-5'-(λ-methacryloyloxypropoxy)-3'-t-butylphenyl]-5-methyl-2H-benzotriazole.

4. An ultraviolet light absorbing intraocular lens comprising a vinyl type copolymer containing from 0.01 to 0.5% by weight of a benzotriazole type ultraviolet light absorbing monomer as chemically bonded therewith and from 0.0001 to 0.1% by weight of a coloring matter, said ultraviolet light absorbing monomer having the formula:

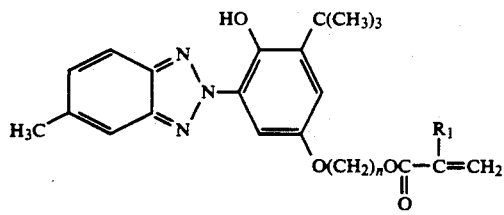

(wherein $R_1$ is H or $CH_3$ and n is 2 or 3).

5. The ultraviolet light absorbing intraocular lens according to claim 4, wherein said ultraviolet light absorbing monomer is 2-[2'-hydroxy-5'-(β-methacryloyloxyethoxy)-3'-t-butylphenyl]-5-methyl-2H-benzotriazole.

6. The ultraviolet light absorbing intraocular lens according to claim 4, wherein said ultraviolet light absorbing monomer is 2-[2'-hydroxy-5'-(λ-methacryloyloxypropoxy)-3 -t-butylphenyl]-5-methyl-2H-benzotriazole.

7. The ultraviolet light absorbing intraocular lens according to claim 4, wherein said coloring matter has a molar absorptivity of at least $2 \times 10^2$ at 480 nm.

8. The ultraviolet light absorbing intraocular lens according to claim 4, wherein said coloring matter has $\lambda_{max}$ at 450 to 510 nm and a molar absorptivity of at least $2 \times 10^3$ at the $\lambda_{max}$.

9. The ultraviolet light absorbing intraocular lens according to claim 4, wherein the amount of said coloring matter is from 0.01 to 0.05% by weight.

* * * * *

UNITED STATES PATENT AND TRADEMARK OFFICE
CERTIFICATE OF CORRECTION

PATENT NO. : 5,147,902

DATED : SEPTEMBER 15, 1992

INVENTOR(S) : MAKOTO ICHIKAWA ET AL

It is certified that error appears in the above-indentified patent and that said Letters Patent is hereby corrected as shown below:

Column 2, line 33, change "$\lambda$" to read --$\gamma$--.

Column 9, line 19, change "$\lambda$" to read --$\gamma$--.

Column 10, line 1, change "$\lambda$" to read --$\gamma$--;
line 59, Claim 3, change "$\lambda$" to read --$\gamma$--.

Column 12, Claim 6, line 5, change "$\lambda$" to read --$\gamma$--.

Signed and Sealed this

Thirty-first Day of May, 1994

Attest:

BRUCE LEHMAN

Attesting Officer

Commissioner of Patents and Trademarks